United States Patent [19]

Galy et al.

[11] Patent Number: 4,716,710

[45] Date of Patent: Jan. 5, 1988

[54] PROCESS FOR THE PREPARATION IN A SERIES OF SELF-INJECTABLE SYRINGES IN A SEALED CONTAINER, FOR LYOPHILIZED MEDICATIONS, AND DEVICE FOR THE IMPLEMENTATION OF SAID PROCESS

[75] Inventors: Michel Galy, Pontchara sur Turdine; Alain Genet, Ecully, both of France

[73] Assignee: Institut-Merieux, Lyons, France

[21] Appl. No.: 880,823

[22] Filed: Jul. 1, 1986

[30] Foreign Application Priority Data

Jul. 1, 1985 [FR] France .................. 85 10009

[51] Int. Cl.$^4$ .................. B65B 31/00; B67B 3/24
[52] U.S. Cl. .................. 53/432; 53/440; 53/485; 29/451; 604/226
[58] Field of Search .................. 29/235, 451; 53/167, 53/476, 287, 485, 432, 489, 433, 403, 440; 604/226, 228

[56] References Cited

U.S. PATENT DOCUMENTS

| | | | |
|---|---|---|---|
| 3,245,194 | 4/1966 | Carski | 53/432 |
| 3,505,775 | 4/1970 | Anderson et al. | 53/489 X |
| 3,696,579 | 10/1972 | Narusawa et al. | 53/440 X |
| 3,737,973 | 6/1973 | Stawski | 29/451 X |
| 3,775,015 | 11/1973 | Tsunoda | 53/432 X |
| 4,022,206 | 5/1977 | Hilleman et al. | |
| 4,213,456 | 7/1980 | Böttger | 604/226 |
| 4,338,764 | 7/1982 | Percarpio | 53/432 |
| 4,447,231 | 5/1984 | Bekkering | 604/226 X |
| 4,543,148 | 9/1985 | Carlson | 604/226 X |

FOREIGN PATENT DOCUMENTS 2319383 2/1977 France .
2556214 6/1985 France .

Primary Examiner—Robert L. Spruill
Assistant Examiner—Steven P. Weihrouch
Attorney, Agent, or Firm—Cushman, Darby & Cushman

[57] ABSTRACT

Process for the preparation in a series of self-injectable syringes characterized mainly by the fact that multiple seal tubes are placed vertically on an appropriate support, that a syringe body is placed vertically in each seal tube, that, into each tubular body thus arranged, a single dose of the medication in solution in a solvent is placed in each seal tube, above the syringe body, a plunger suspended by its pusher in a movable manner, at the lower end of a stopper which can adapt to the seal tube, so that said plunger is essentially in the axis of the syringe body and the lower end of said plunger is located above the upper end of the syringe body, with said stopper being held in a position so that said seal tube is not blocked or is not entirely blocked, to thus obtain an assembly constituting an open system in which the internal space, in the seal tubes and above said solution in the syringe bodies, is connected with the outside of the system, that the lyophilization operation is effected and, at this time, downward vertical pressure applied to the stoppers so that said stoppers completely block said seal tubes while said plungers, fastened to said stoppers, are introduced into the tubular bodies until the predetermined maximum insertion position is reached; a device and stopper for the implementation of said process.

7 Claims, 7 Drawing Figures

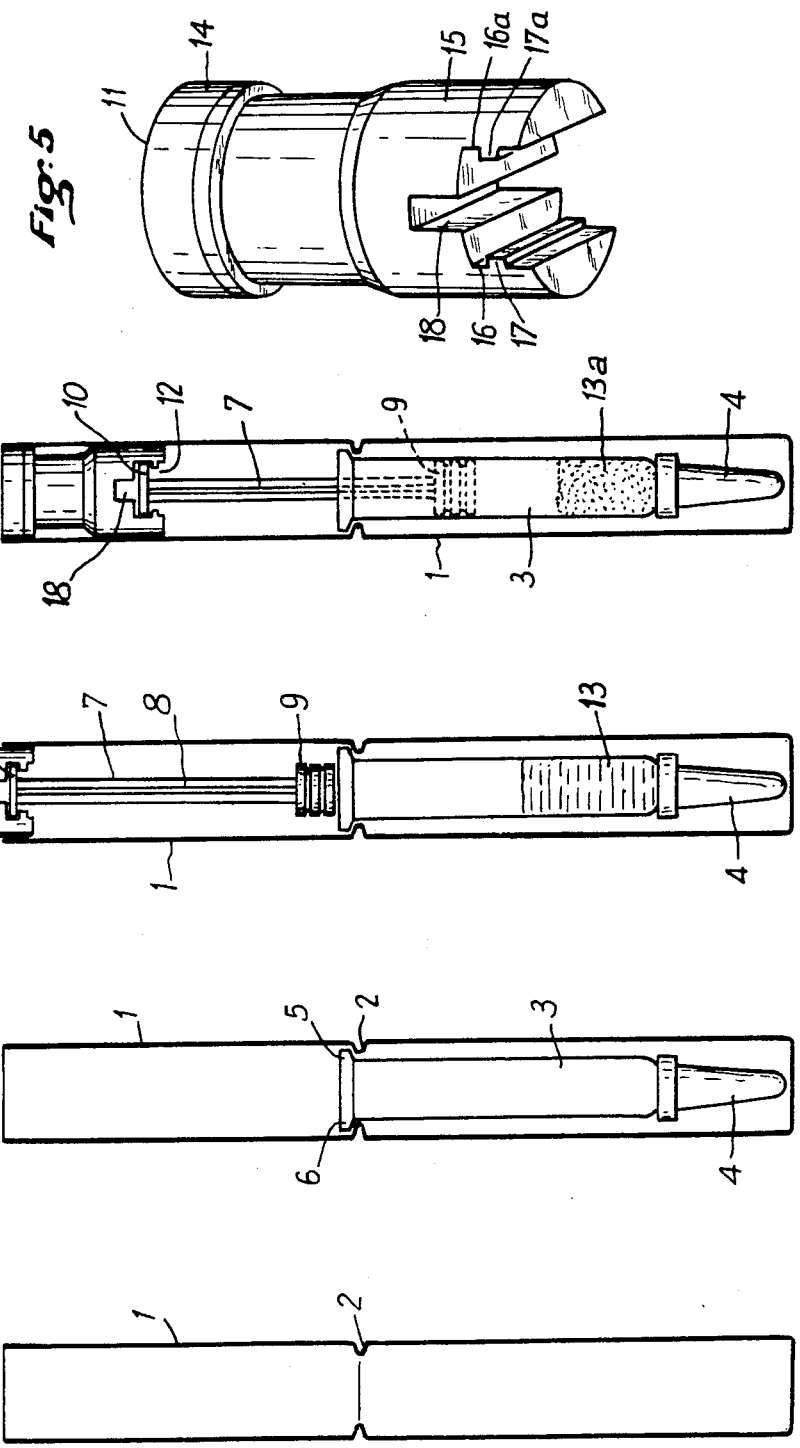

PROCESS FOR THE PREPARATION IN A SERIES OF SELF-INJECTABLE SYRINGES IN A SEALED CONTAINER, FOR LYOPHILIZED MEDICATIONS, AND DEVICE FOR THE IMPLEMENTATION OF SAID PROCESS

The present invention relates to a process for the preparation in a series of self-injectable syringes for lyophilized medications, arranged in a sealed container, as well as a device for the implementation of said process.

Lyophilized vaccines are already known which are provided in the form of single doses in a self-injectable container, with this container being a flexible tube constituting a self-injectable syringe without a plunger; see U.S. Pat. No. 4,022,206.

The preparation in a series of self-injectable syringes containing a lyophilized medication presents problems difficult to resolve due to the fact that the lyophilization must take place while the syringes are open, and the closing of the syringes with plungers creates problems due to the presence of a gas trapped in the syringe, which, in practice, requires this closing to be done in the lyophilization device itself.

Other problems stem from the fact that the lyophilized product is protected only by the lower end of the plunger, which also acts as a stopper. But, because it is used as a plunger, this stopper-plunger must have a low degree of adhesion to glass and thus provides only a limited seal.

However, the lyophilized product in the syringe is very hygroscopic. Thus, a treatment must be provided for the syringe, which ends in a glass tube closed by a desiccant stopper.

Nonetheless, experience has shown that, in certain cases, the lyophilizate is more hygroscopic than the desiccant stopper and the moisture potentially introduced when the syringe is packaged in said tube can, in the long term, enter the syringe and alter the lyophilized product.

The present invention relates to a process allowing these problems to be remedied and allowing the production of self-injectable syringes containing a lyophilized medication, arranged in a sealed container, using simple operations effected under the best conditions of homogeneity and sterility.

An important characteristic of the process according to the invention is that the syringe is already arranged in the container during the lyophilization and that the sealing of syringe and the container is effected inside the lyophilization device itself, at the end of the lyophilization operation.

The present invention relates to a process for the preparation in a series of self-injectable syringes for lyophilized medications, said syringes being arranged in a sealed tube, the said syringe being of the type comprising a tubular body whose lower end is adapted to accommodate an injection needle, and a plunger comprised of a shaft whose lower end comprises a part having an enlarged section which can slide with friction inside said tubular body and whose upper end comprises an extended edge forming a pusher, characterized by the fact that:

the lower ends of said tubular bodies are sealed using movable seal means;

multiple seal tubes are placed vertically on an appropriate support, which holds them so that their upper open ends are essentially at the same level, with said seal tubes being large enough so that they can contain the syringe - plunger combination;

a syringe body is placed vertically in each seal tube;

said syringe body is held so that the seal tube and the syringe body which it contains are arranged in an essentially coaxial manner;

a single dose of the medication in solution in a solvent is introduced in each tubular body thus arranged;

a plunger suspended by its pusher is arranged in each seal tube, above the syringe body, in a movable manner, at the lower end of a stopper which can adapt to said seal tube, so that said plunger is essentially in the axis of the syringe body and the lower end of said plunger is located above the upper end of the syringe body, with said stopper being held in a position so that said seal tube is not blocked or is not entirely blocked, to thus obtain an assembly comprising an open system in which the internal space, in the seal tubes and above said solution in the syringe bodies, is in communication with the outside of the system;

said system is introduced into a lyophilization device;

the lyophilized operation is effected;

an inert gas is introduced into the lyophilization device at a predetermined pressure which is lower than atmospheric pressure;

then, a downward vertical pressure is applied to said stoppers, so that said stoppers completely block the seal tube while the said plungers, fastened to said stoppers, are introduced into said tubular bodies until a predetermined maximum insertion position is reached;

and subsequently, said inert gas is introduced into the lyophilization device until the pressure reaches atmospheric pressure.

In specific embodiments, the process according to the present invention can still exhibit the following characteristics, taken singly or in combination:

syringe bodies are utilized, whose upper part comprises a widened neck forming holding lugs, in combination with seal tubes provided with an annular restriction at a level such that the said syringe bodies are suspended and held properly centered in the seal tube due to the contact of said lugs with said annular restriction;

said vertical pressure is applied using an internal jack with which is fitted the lyophilization equipment.

The present invention also relates to a device intended for the implementation of the aforementioned process.

This device essentially comprises seal tubes provided with an annular restriction located a distance from the bottom of the tube slightly greater than the length of the tubular syringe body provided with said movable blocking means, the said seal tubes having a total length sufficient to contain the syringe bodies over which the plunger thereof has been mounted.

In the preferred embodiments, the device also comprises stoppers having special shapes for the said seal tubes, the said stoppers comprising means so that said pusher can be housed and thus the plunger can be temporarily engaged, keeping it suspended under the stopper.

In addition, the stopper can be provided over part of its length, except in the area near its upper end, with at least one vertical slot which connects the inside of the seal tube to the outside, even when said stopper is partially inserted, by its lower part, in the seal tube.

The invention also relates to a stopper intended for the implementation of the above described process. This stopper comprises means allowing the engagement and holding in suspension of the upper end, comprising an enlarged part, of a plunger shaft, and that it also comprises, on a part of its length, except in the area near its upper end, at least one longitudinal slot connecting the area near the lower part of the stopper with the external surroundings of a median part of said stopper.

The stopper, having a general cylindrical shape, comprises a body having a diameter which is essentially equal to the diameter of the seal tube, the said body being generally overmounted by an enlarged part intended to rest outside of the seal tube and allowing the stopper to be grasped so that it can be removed when the syringe is used.

To connect the tube to the outside, the stopper can, for example, comprise either a longitudinal slot or two diametrically opposite longitudinal slots.

The cylindrical surface of the stopper intended to enter into contact with the seal tube can comprise one or several annular flanges intended to improve the seal.

In a specific embodiment, the stopper comprises at its lower end a transverse slot having a shape complementary to that of the pusher, with this transverse slot allowing the engagement and holding in suspension of the enlarged part, forming the pusher, of the upper end of the plunger shaft. In this case, the longitudinal slot can be made as an extension of said transverse slot.

In another embodiment, the stopper comprises in its lower part an axial cylindrical recess whose diameter is essentially the same as that of the pusher. This recess is made over a height which is slightly greater than that of the longitudinal slot with which is it connected. During use, the upper part of the plunger is pushed into the recess until the pusher comes into contact with the bottom of the recessed part. The bottom of the recessed part can be provided with a circular lateral groove intended to promote the engagement of the pusher.

Finally, it will be noted that the stopper can be made in two parts, of two different materials: for example, an upper part, made of rubber, so as to promote the seal, and a lower part, made of a more rigid synthetic material, so that the plunger can be best guided during its introduction into the syringe body.

The invention will now be described in greater detail, with reference to the specific embodiments described in the attached drawings, in which:

FIG. 1 is a schematic cross section view of a seal tube;

FIG. 2 is a schematic cross section view of a seal tube in which the syringe body is placed;

FIG. 3 is a schematic cross section view analogous to that in FIG. 2, in which the seal tube is also provided with a stopper to which a plunger is attached, with said stopper being shown in the position it occupies during the lyophilization operation;

FIG. 4 is a schematic cross section view analogous to that in FIG. 3, but in which the stopper is shown in the position in which it blocks the seal tube, the position it occupies after the lyophilization operation;

FIG. 5 is a perspective view of a specific embodiment of the stopper for the seal tube.

Figure 6:
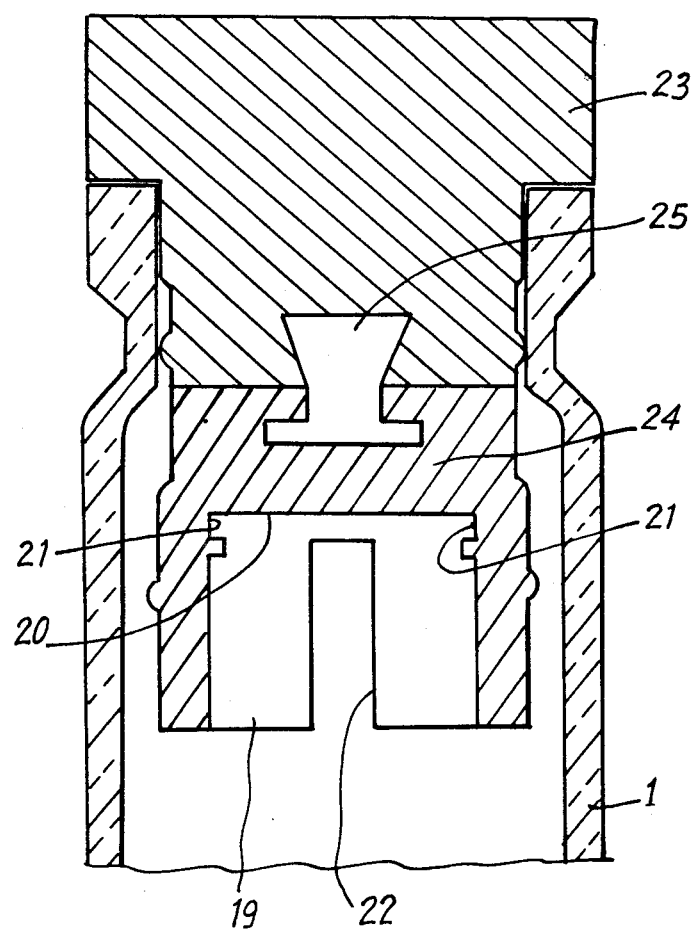
FIGS. 6 and 7 are axial cross section views of two other embodiments of the stopper.

The drawings show that the seal tube 1 having its upper end open is provided, essentially at the mid-height thereof, with an annular restriction 2. The syringe body 3, provided at its lower end with a movable seal device 4, which is known in and of itself, comprises at its upper end an enlarged part in the form of a flange constituting the holding lugs 5, 6, which come into contact with the annular restriction 2, so that the syringe body 3 is suspended and correctly centered in the seal tube 1.

The plunger 7 is comprised of a shaft 8 provided at its lower end with a part 9 having enlarged section which can slide with friction inside the syringe body 3. The plunger is provided at its upper end with an enlarged part forming pusher 10.

The stopper 11 comprises at its lower end a slot 12 allowing the temporary engagement of the plunger 7 by its pusher 10. This slot comprises a vertical extension 18 in the upward direction.

The device operates as follows:

The syringe bodies 3 provided with their blocking means 4 are placed in the tubes 1. The syringe bodies are thus suspended and correctly centered due to the contact of the lugs 5, 6 with the annular restriction 2.

The seal tubes containing the syringe bodies are placed in an appropriate support (not shown) and the assembly is sterilized according to the usual methods.

Next, according to known methods, single doses of the medication solution 13 are distributed into each syringe. The assembly comprised of the stopper 11 and the plunger 7, is next placed above the syringe, in the position shown in FIG. 3. It is noted that the stopper 11 is only partially inserted into the tube 1 and that the slot 18 allows communication of the inside of the tubes 1 and 3 with the outside.

The glass tubes thus equipped are introduced into a lyophilization machine (not shown). The lyophilization is effected in a conventional manner.

In FIG. 4, reference 13a designates the lyophilizate obtained after the lyophilization is completed.

At the end of the operation, a sealing system comprised of a jack (not shown) lowers the the stoppers 11 carrying plungers 7. The plungers 7 which are fastened to the stoppers 11 are then introduced into the syringe bodies 3, and thus block the syringe while at the same time the stoppers 11 completely block the seal tubes 1, as shown in FIG. 4.

Thus, the entire operation is effected under the dehydrating conditions existing in the lyophilization device after the lyophilization is completed, which prevents any incorporation of parasite moisture.

When implemented, the user takes out the stopper-syringe assembly by removing the stopper 11 which is, for example, made of rubber.

He next detaches the syringe from the stopper, and then utilizes the syringe, in which the lyophilizate 13a is perfectly preserved, under the usual conditions for the use of such syringes.

As seen in the embodiment in FIG. 5, the stopper 11 having a general cylindrical shape comprises at its upper end a part having an enlarged section 14 which ensures the sealed closing of the tube 1, and at its lower end, another part having enlarged section 16, allowing the stopper to be kept in a stable position when it is only partially inserted into the tube (FIG. 3).

On the other hand, the stopper 11 comprises at its lower end a transverse slot 12 having a diametral direction especially comprising an indented part 16, 16a, constituting a housing for the pusher 10 of the plunger 7, the said pusher being held by the projected part 17, 17a, on which it rests. The slot 12 is extended upwards by the slot 18, whose function has been indicated above.

It is seen that the special shape of the stopper 11 allows a temporary engagement of the plunger 7, a temporary positioning at the top of the tube 1 (FIG. 3), during the lyophilization, assuring the passage of the water vapor to the outside, and thus, after the stopper is inserted, allows a satisfactory seal for the stopper 11-tube 1 assembly.

FIG. 6 shows another embodiment for the stopper, inserted into the seal tube 1 (only its upper end is shown). The lower part of the stopper comprises a recess 19, the bottom 20 of which is provided with a lateral circular groove 21 intended to promote the engagement of the pusher. FIG. 6 shows one of the two diametrically opposed longitudinal slots 22, intended to allow communication between the inside and the outside of the seal tube during the lyophilization. The stopper in FIG. 6 is made in two parts, the upper part 23 being made of rubber and the lower part 24 being made of a more rigid synthetic material. The upper part 23 comprises an annular seal flange 25. The two parts 23 and 24 can be assembled by snapping on a rigid connector, for example, and made of metal, occupying the hollow part 25. It is seen that the shape of the upper end of the seal tube 1 permits seating with a conventional tearable capsule.

Figure 7:
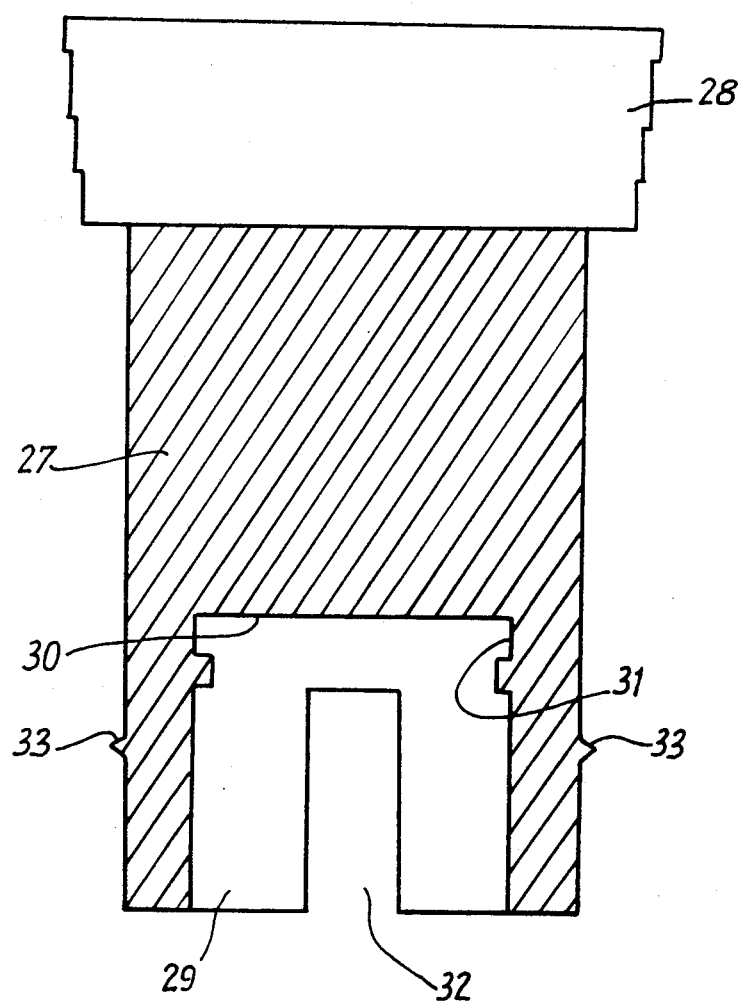

The stopper of FIG. 7 is similar in its conception to the stopper of FIG. 6, but it is made of a single part. This stopper, made of rubber, comprises a cylindrical body 27 having a section such that is can slide with slight friction in the tube 1 (not shown). The upper end is constituted by a part having enlarged section 28. The lower part comprises a cylindrical central recess 29 having near the bottom 30, a circular lateral groove intended to improve the engagement of the pusher. Finally, the lower part comprises two diametrically opposed longitudinal slots such as slot 32 shown in FIG. 7. At a level situated between the upper end of the slot 32 and the lower end of the stopper, the body 27 is provided with a seal flange 33. This flange can be lacunar or even replaced by a few lugs regularly distributed on the circumference of the stopper.

The flange 33 permits to easily regulate the intermediate lowering position and stopper in tube 1 before lyophilization. To lower the stopper more, beyond the flange 33 it is necessary to exercise a clearly more significant force. Moreover, the flange 33 assures holding the stopper in the intermediate position during lyophilization.

The flange 33 can be discontinuous or can be replaced by a few lugs disposed on a circular line parallel to the base of the stopper.

What is claimed:

1. Process for the preparation in a series of self-injectable syringes for lyophilized medications, arranged in a sealed tube, each of said syringes comprising a tubular body whose lower end is adapted to accommodate an injection needle and a plunger comprising a shaft, whose lower end is provided with a part having an enlarged section capable of sliding with friction inside said tubular body and whose upper end comprises an enlarged end forming a pusher, said process comprising:
    sealing the lower ends of said tubular bodies using movable seal means;
    vertically disposing multiple seal tubes on an appropriate support, which holds them so that their upper open ends are essentially at the same level, the said seal tubes being large enough so that they can contain the syringe-plunger assembly;
    vertically disposing a syringe body in each seal tube;
    maintaining the said syringe body in a manner such that the seal tube and the syringe body which it contains are arranged in an essentially coaxial manner;
    introducing a single dose of the medication in solution in a solvent in each tubular body thus arranged;
    disposing a plunger suspended by its pusher in each seal tube, above the syringe body, in a movable manner, at the lower end of a stopper which can adapt to said seal tube, so that said plunger is essentially in the axis of the syringe body and the lower end of said plunger is located above the upper end of the syringe body, with said stopper being held in a position so that said seal tube is not blocked or is not entirely blocked, so as to obtain an assembly comprising an open system in which the internal space, in the seal tubes and above said solution in the syringe bodies, communicates with the outside of the system;
    introducing said system into a lyophilized device;
    effecting a lyophilization operation;
    introducing an inert gas into the lyophilization device at a predetermined pressure which is lower than atmospheric pressure;
    applying a downward vertical pressure to said stoppers, so that said stoppers completely block the seal tubes while said plungers fastened to said stoppers, are introduced into said tubular bodies until a predetermined maximum insertion position is reached; and subsequently, introducing said inert gas into the lyophilized device until the pressure reaches atmospheric pressure.

2. The process according to claim 1 wherein said syringe bodies have an upper part comprising holding lugs in combination with seal tubes provided with an annular restriction at a level such that said syringe bodies are suspended and maintained properly centered in the seal tube by the contact of said lugs with said annular restriction.

3. The process according to claim 1 wherein said vertical pressure is applied using an internal jack with which the lyophilization equipment is provided.

4. The the process of claim 1 including providing said seal tubes with an annular restriction at a distance from the bottom of the tube which is slightly greater than the length of the tubular syringe body provided with movable seal means, said seal tubes having a total length which is sufficient to contain the syringe bodies over which their plunger has been mounted.

5. The device according to claim 4, in which said stoppers comprising at their lower ends means allowing said pusher to be housed and thus to allow the plunger to be temporarily engaged while keeping it suspended under the stopper.

6. The process according to claim 5 wherein said stoppers also include, over a part of their length, except in the area near their upper end, a vertical slot connecting the inside of the seal tubes with the outside.

7. The process according to claim 1, in which the stopper comprises in its lower part either a transverse slot or an axial recess, whose shape allows the engagement and holding in suspension of the enlarged part, forming a pusher, of a plunger shaft, and, over a part of its length, except in the area near end, a longitudinal slot, which allows communication of the area near the lower part of the stopper with the area near the outside of a median part of said stopper.

* * * * *